US008667290B2

(12) United States Patent
Appelbaum et al.

(10) Patent No.: US 8,667,290 B2
(45) Date of Patent: Mar. 4, 2014

(54) EFFICIENT, HIGH VOLUME DIGITAL SIGNATURE SYSTEM FOR MEDICAL AND BUSINESS APPLICATIONS

(76) Inventors: Joel Appelbaum, Gainesville, FL (US); Robert Yancey, Gainesville, FL (US)

( * ) Notice: Subject to any disclaimer, the term of this patent is extended or adjusted under 35 U.S.C. 154(b) by 0 days.

(21) Appl. No.: 13/560,600

(22) Filed: Jul. 27, 2012

(65) Prior Publication Data

US 2013/0185565 A1 Jul. 18, 2013

Related U.S. Application Data

(60) Provisional application No. 61/513,506, filed on Jul. 29, 2011.

(51) Int. Cl.
*H04L 29/06* (2006.01)

(52) U.S. Cl.
USPC ............................. 713/176; 726/26; 726/30

(58) Field of Classification Search
None
See application file for complete search history.

(56) References Cited

U.S. PATENT DOCUMENTS

| | | | |
|---|---|---|---|
| 6,904,416 B2 * | 6/2005 | Nassiri | 705/51 |
| 2005/0138382 A1 * | 6/2005 | Hougaard et al. | 713/176 |
| 2008/0030800 A1 * | 2/2008 | Matsukawa et al. | 358/474 |
| 2008/0209313 A1 * | 8/2008 | Gonser | 715/255 |
| 2009/0024912 A1 * | 1/2009 | McCabe et al. | 715/224 |
| 2010/0121854 A1 * | 5/2010 | Fischer | 707/737 |
| 2010/0328701 A1 * | 12/2010 | Silverbrook et al. | 358/1.14 |
| 2011/0213700 A1 * | 9/2011 | Sant'Anselmo | 705/39 |
| 2011/0314371 A1 * | 12/2011 | Peterson et al. | 715/234 |
| 2012/0086971 A1 * | 4/2012 | Bisbee et al. | 358/1.14 |
| 2012/0136776 A1 * | 5/2012 | Haberaecker et al. | 705/38 |
| 2012/0257249 A1 * | 10/2012 | Natarajan | 358/1.15 |
| 2013/0159720 A1 * | 6/2013 | Gonser et al. | 713/176 |

OTHER PUBLICATIONS

PCT/US12/48432, Mercury Authentications, Inc., et al., Written Opinion of the International Searching Authority.
PCT/US12/48432, Mercury Authentications, Inc., et al., International Search Report.

* cited by examiner

*Primary Examiner* — Jeffery Williams

(57) ABSTRACT

The system relates to a method for collecting signatures from pre-validated signers. In one aspect of the method, a pre-validated signer's signature is affixed to an electronic document in an appropriate location after the pre-validated signer authorizes the use of his or her signature.

10 Claims, 22 Drawing Sheets

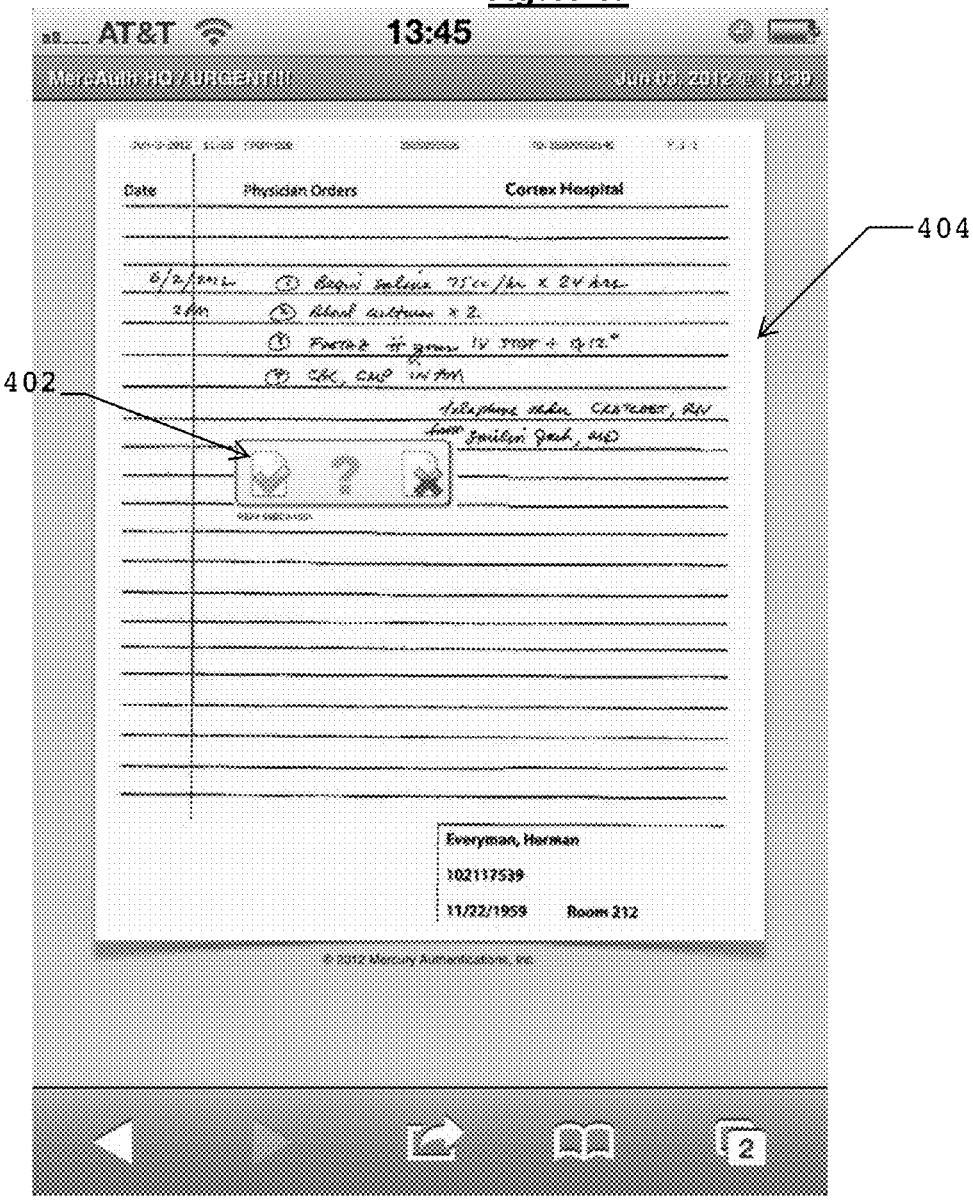

Note that an image of the signer's actual signature is digitally inserted. The time and date stamp as well as the document number will appear along with the signature on the stored document.

Note that the archived document includes time, date, and document number within the signature box.

EFFICIENT, HIGH VOLUME DIGITAL SIGNATURE SYSTEM FOR MEDICAL AND BUSINESS APPLICATIONS

CROSS-REFERENCE TO RELATED APPLICATION

This application claims priority to provisional application 61/513,506, filed Jul. 29, 2011, the entire contents of which are incorporated herein by reference.

BACKGROUND OF THE INVENTION

1. Field of the Invention

This invention relates to methods and systems for obtaining efficient, high volume certified digital signatures, which may be suited for use in business, medical, legal, engineering, and other applications.

2. Description of the Background Art

Presently, authorizing signatures are a necessary part of the work environment. Timed and dated authorizations or orders, a clear sequence of responsibility, are needed in engineering, legal, business, financial, and medical operations. Often obtaining these signatures is an efficiency limiting factor in these processes; be it for a purchase order, authorization to begin an engineering procedure, singing a contract, or medical orders.

One of these work environments is the medical environment where large numbers of timely secure physician authorizations are necessary for patient care, billing procedures, medicolegal protection, and reviews by certifying agencies. Often dozens, or even more than 100 provider (physician) signatures are needed per day per medical facility. One problem that may arise is that often the signer is in a remote location. Obtaining these signatures reliably is time consuming for the provider and troublesome for the administrations of medical facilities.

Timely confirmation of medical orders is considered an important patient safety measure by The Joint Commission of Accreditation of Healthcare Organizations (JCAHO) and the Center for Medicaid and Medicare Services (CMS). Similarly, in the business, legal, engineering, and financial environments, obtaining timely, legally verifiable signatures is often a procedural rate limiting step; be it for a purchase order, a contract to be signed, or an engineering procedure to be authorized.

Current commercially available internet based digital signature systems, such as DocuSign, Echosign, and AgreenSign, are not intended for efficient high volume authorizations. These services may be slow and somewhat complex to use for the casual user. Security certificates of digital signatures may be weak. They do not use two-factor user identification and generally rely on insecure means such as unencrypted email for transmission of important documents. Furthermore, these services are not optimized for efficient smartphone or other mobile device use. While Xyzmo.com is oriented to smartphones, its usage may be cumbersome and document security and verifiability is suboptimal. None of these services are properly sequenced for efficiency, security, and ease of use. Rather, these solutions are intended for episodic use by specifically trained clerical personnel.

The majority of skilled nursing facilities, assisted living facilities, and many long term acute care hospitals still use paper systems and will not be converted to fully electronic medical records for years, if ever. Freestanding medical service centers such as physical therapy, surgicenters, and outpatient rehabilitation centers need physician signatures for billing and documentation purposes. Homecare agencies, infusion pharmacies, durable medical equipment agencies also often use electronic systems for tracking billing and medical documentation. All of these agencies or facilities generate thousands, even multiples of tens of thousands of signature requests of providers per year. Most commonly, these remote signatures include telephone orders related to direct patient care, review of critical new patient information such as laboratory data or radiology data, confirming plans of care, and certifying patients' needing hospitalization, transfer, or placement in a facility. Obtaining these authentications is troublesome and time consuming process for both the medical organization and for the provider.

Efforts to fax paper copies of these important documents for signature to a physician's office or emailing the documents to the physician have not successfully addressed the problem. Often days or weeks go by before the provider signs the document. He/she often doesn't time and date the signature. Time shuffling papers and faxing is required of the provider's office personnel and of the personnel of the requesting facility. A simple efficient method to accomplish this task is needed.

Patient safety organizations such as JCAHO recommend that telephone orders and critical labs be reviewed within 48 hours but that simple goal has not been achieved often and is widely considered impractical. Clearly, 48 hour delays for review of potentially harmful orders and urgent patent information is not adequate either. What is needed is a near realtime review by the provider no matter where the provider is.

Medical informatics has special security requirements to guard and keep confidential personal health information (PHI). The Health Insurance Portability and Accountabilty Act of 1996 (HIPAA) has strict requirements as to how PHI can be safely and securely handled for the patient. Any instrument used to review patient data or orders must comply with these requirements.

Electronic Medical Record systems (EMR) are rapidly coming into use in acute care hospitals because the HITECH Act actually requires them to adopt EMR and actually pays them to do so. Many of these systems are admirably secure and comprehensive but they do not address the need for remote, rapid, efficient, high volume digital signatures. They may require the provider to sign in via a remote terminal. During most of the day physicians are not sitting in front of a computer and therefore the need is unmet. However, most North American physicians now use mobile devices with internet access which are with them all day. A method that allows them to promptly review and sign from these mobile device is needed.

The High Volume Digital Signature System ("HVDSS") described here is a novel solution to the problems described above both in the medical environment and in the other cooperative activities such as engineering projects, corporate executive procedures, and business contracts and communications. The solutions described here exist in both a paper-to-digital form as well as a fully electronic form.

Therefore, it is an object of this invention to provide an improvement which overcomes the aforementioned inadequacies of the prior art devices and provides an improvement which is a significant contribution to the advancement of the electronic or digital signature art.

Another object of this invention is to provide a high-volume digital signature system which improves the efficiency and workflow of obtaining digital signatures.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing this invention, the invention comprises a High Volume Digital Signature System which improves the efficiency and workflow of obtaining digital signatures in the business, engineering, legal, or medical environment in which large numbers or especially rapid digital signatures are required. The prototype is the medical environment in which nursing homes, hospitals, homecare services, or free-standing medical service centers need a high volume of prompt, secure signatures from medical providers.

The HVDSS works in part via a pre-validated, closed network of designated signers which allows an efficient and secure routing. The system may also allow convenient viewing and rapid signing of documents.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIGS. 4a-g depict a series of interfaces which may be presented to a pre-validated signer in accordance with one embodiment of the present disclosure.

FIG. 8 illustrates a label design interface in accordance with one embodiment of the present disclosure.

Similar reference characters refer to similar parts throughout the several views of the drawings.

DETAILED DESCRIPTION OF THE PREFERRED EMBODIMENT

Figure 1:
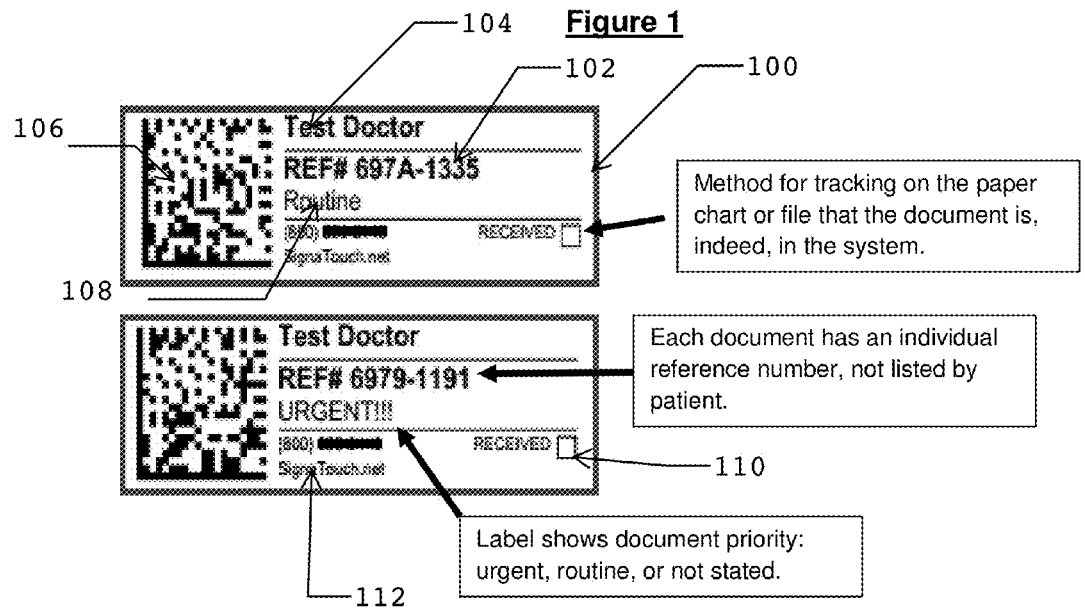
FIG. 1 depicts 2D barcode stickers in accordance with an embodiment of the present disclosure.

FIG. 1 depicts labels 100 which may be used in accordance with an embodiment of the present disclosure. The labels 100 may preferably include a unique identifier 102, a signer's name 104, a machine readable identifier 106, and a priority 108. The barcode label may also include a tracking method 110 and other information 112.

The label 100 is preferably affixed to a paper document which requires a signature. Preferably, the label 100 is affixed on the document in the location in which a signature is desired. The unique identifier 102 may be stored in a datastore, such as a database. The unique identifier 102 may be used to uniquely identify the respective document to which the label 100 has been affixed.

The machine readable identifier 106 may be any machine readable indicia, such as a barcode, 2D Matrix barcode (as illustrated), a datamatrix code, a QR code, or the like. The machine readable identifier 106 is used when the document is scanned to assist in determining the appropriate routing of the document to gather the necessary signature(s).

The label 100 may also include priority information 110. The priority information 110 may be used to indicate to the signer that the document to be signed requires immediate attention, or some other priority related information.

Figure 2:
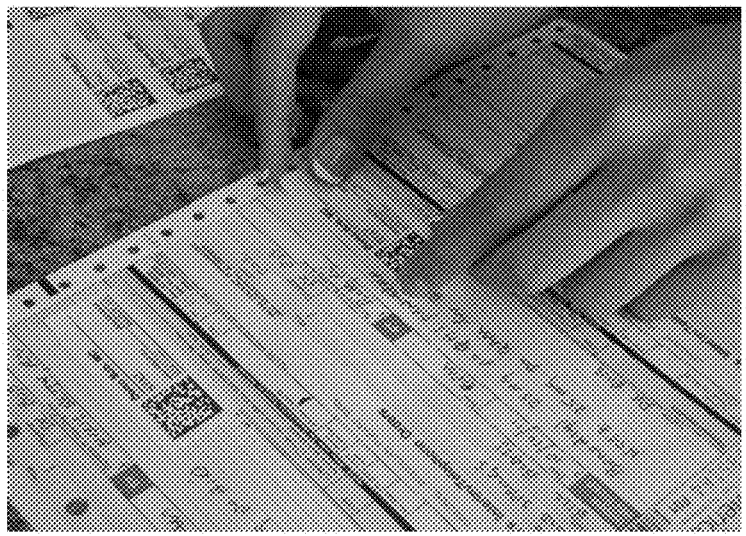
FIG. 2 depicts a 2D barcode being affixed to a document in accordance with one embodiment of the present disclosure.

FIG. 2 depicts a label 100 being affixed to a document requiring a signature. Notably, the label 100 is affixed in the location where a signature would normally be affixed. Thus, when an electronically stored signature is affixed on the electronic copy of the document (after authorization from the pre-validated signer, as discussed below), the electronically stored signature may be placed geographically within the document in an appropriate location corresponding to the signature's intended location. Thus, there is no need to store templates or the like for documents to be signed because the location information for where the signer's signature should be placed may be determined from the location of the label 100.

Once the label 100 is affixed to the document, the document may be submitted to a device of a pre-validated signer by operation of a method in accordance with the present disclosure. In one embodiment, the document may be scanned into a computing system. The scanning operation may review the label and determine from the machine readable identifier 106 the appropriate routing for the document.

In a preferred embodiment, a datastore stores a mapping between the document identifier and the pre-validated signer. When the document is scanned, the machine readable identifier 106 is analyzed by the computing process, which looks up the unique identifier 102 indicated on the label 100. In another embodiment, the machine readable identifier 106 contains the same information as the unique identifier 102 in a machine readable format. In yet another embodiment, the scanning process scans the unique identifier 102 and performs character recognition, such as Optical Character Recognition, to determine the unique identifier 102.

Once the unique identifier 102 is determined, the system may lookup the appropriate signer to direct the document to in accordance with the present disclosure.

In another embodiment, documents to be signed need not be scanned. Instead, such documents may be generated electronically, for instance from a computer workstation. In one example of such an operation, a specialized print driver is configured on the work station so that when a user prints the desired document to the specialized print driver, the document is automatically routed in the system in accordance with the present disclosure. In such an embodiment, the user may also optionally be presented an opportunity to define where in the document the electronic signature should be placed.

Figure 3:
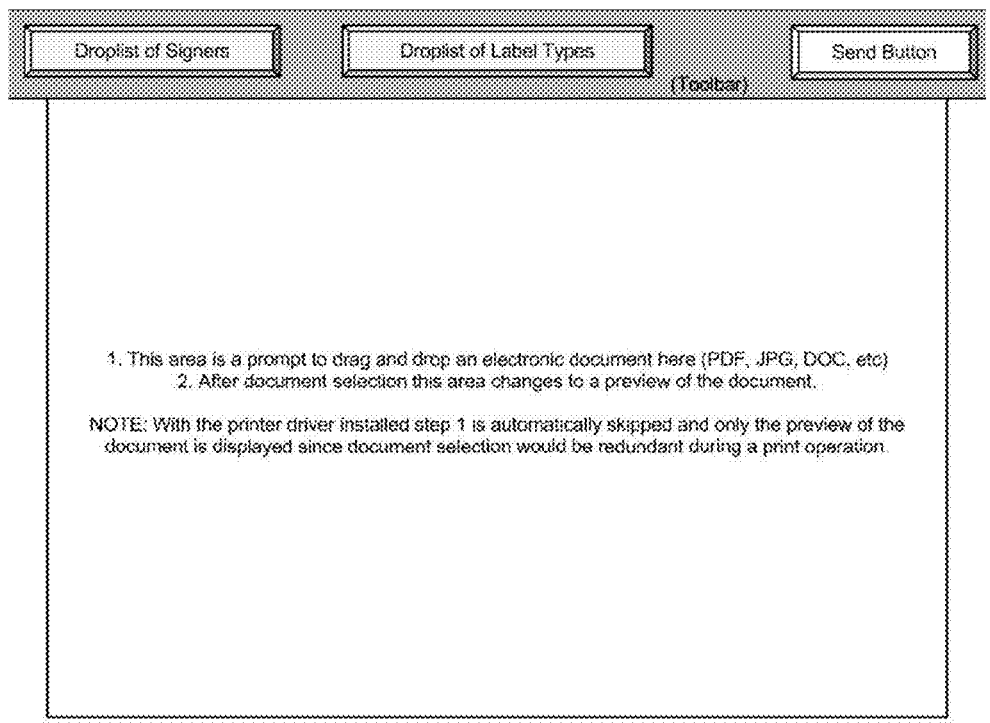
FIG. 3 depicts an exemplary user interface for the document routing system in accordance with one embodiment of the present disclosure.

In another example of such an operation, a user may drag and drop electronic files (for instance PDFs, word processing documents, etc.) into the system. FIG. 3 depicts an illustrative example of an interface to permit a user to add additional electronic documents into a system in accordance with the present disclosure. Through this interface, after a document is loaded, a user may designate where the signature is to appear on the final signed electronic document.

Once a document is in the system to be signed, it must be routed to one or more pre-validated signers. FIGS. 4a through 4g depict illustrative interfaces that may be displayed to a pre-validated signer enabling the pre-validated signer to review the respective document and either sign it or reject it.

When a document is ready to be signed, a notification is preferably sent to the signer. The notification may be sent instantly, or may be scheduled for some later delivery period. For instance, notifications may be sent only once a day, hourly, or other preconfigured time period. Additionally, a signer may be permitted to specify any desired schedule during which she or he wishes to receive signature requests.

In one embodiment, the priority 108 associated with a document may be used in determining an appropriate notification timing sequence. For example, the system may be configured to enable high priority 108 documents to be delivered immediately, while leaving routine documents for a later delivery schedule.

As mentioned earlier, when a signer registers with the system, the signer indicates a device through which the signer is willing to utilize the system. The device may be any device which can be communicatively coupled with the system. Preferably, the device is a smartphone. The device may also be a computer, a fax machine, an IP address, or the like. Each device the signer wishes to utilize with the system should be pre-registered with the system.

Figure 4A:
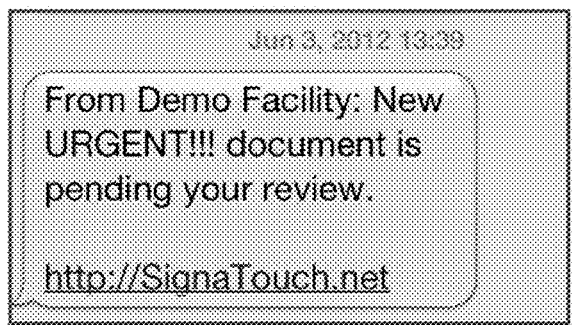

FIG. 4a depicts an exemplary notice that may be sent to a device by way of an SMS text message. Notifications may be sent through any reasonable mechanism, including SMS text messages, emails, and automated phone calls. As depicted in FIG. 4a, the signer is notified that a document is available which requires the signer's signature.

Figure 4B:
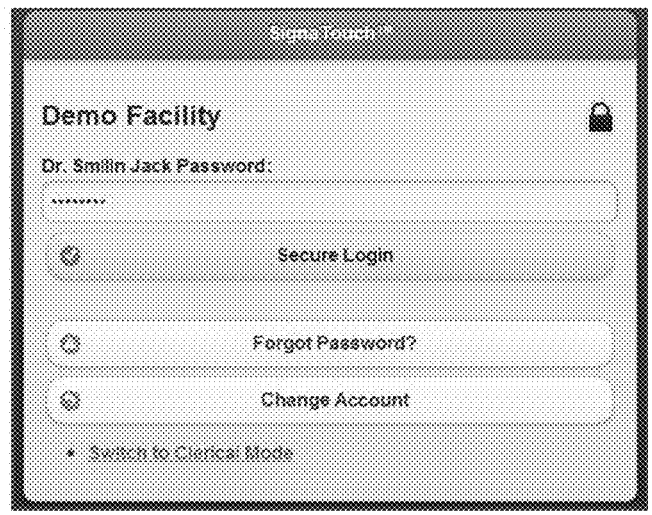

Clicking on the link in FIG. 4a may present the signer with an interface as depicted in FIG. 4b. As shown in FIG. 4b, the signer is given an opportunity to log into the system by providing appropriate credentials.

Figure 4C:
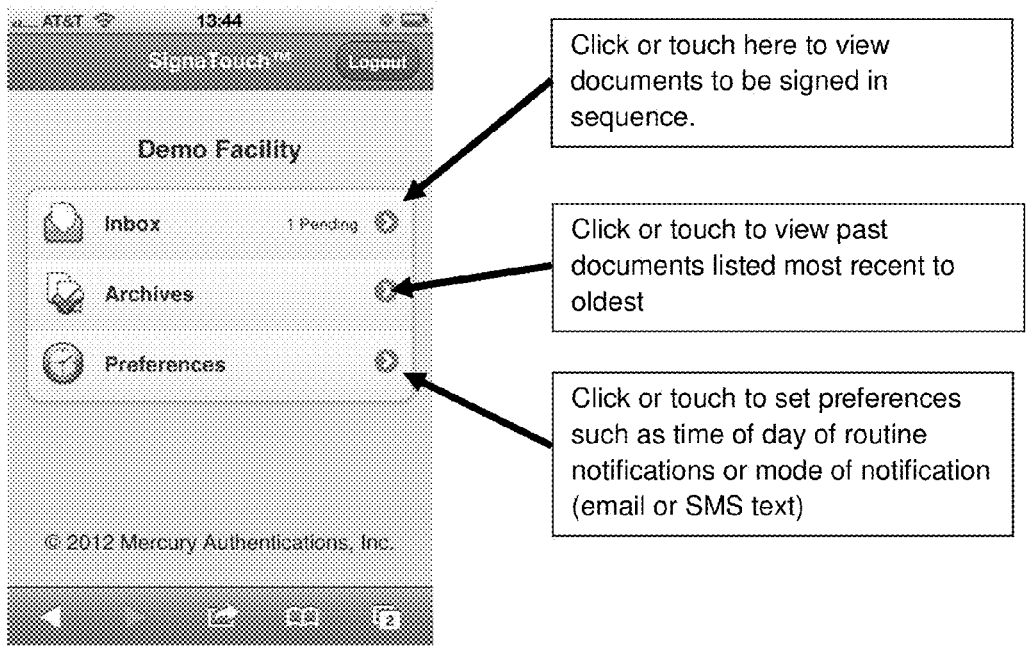

Once authenticated, the signer is presented with pending signature requests, as depicted in FIG. 4c. In one embodiment, the signer may also review archived signatures and configure other preferences.

FIG. 4d shows an exemplary screen asking the signer to authorize a signature on the respective document. Preferably, if the document to be signed was originally a paper document, the signature authorization buttons 402 are depicted in the image 404 in the location in which the label 100 was affixed. If the document to be signed was originally an electronic document, the signature authorization buttons 402 are preferably depicted in the image 404 in the location in which the user configured the signature region to appear.

Figure 4E:
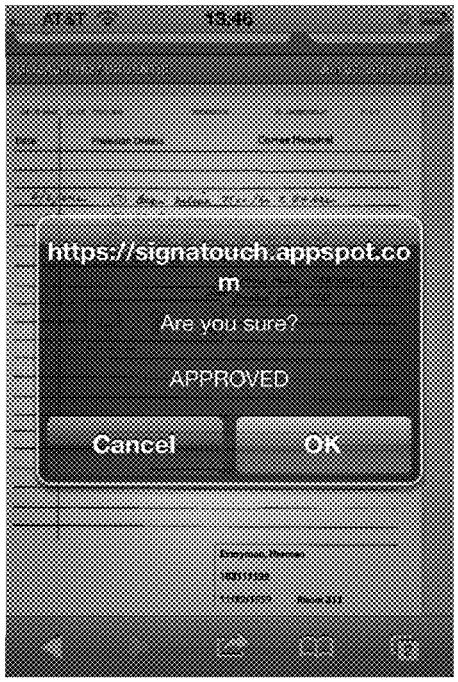
Figure 4F:
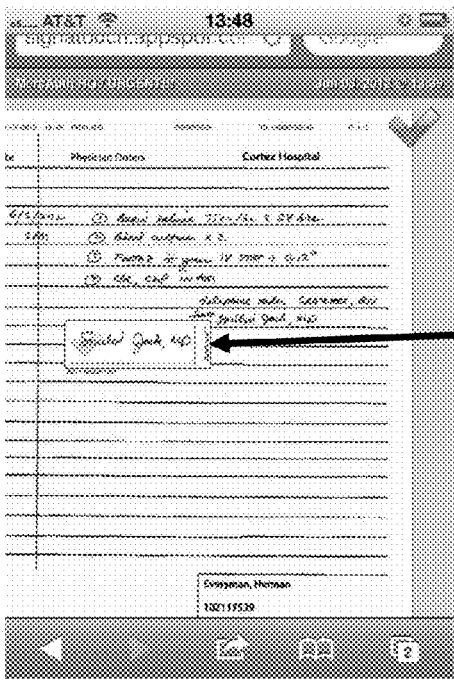

If the signer approves of the signature, she or he may click the appropriate approval button. Optionally, the system may present a confirmation screen as depicted in FIG. 4e. If the user confirms the authorization, an image of the signer's actual physical signature is affixed to the electronic document. In a preferred embodiment, as shown in FIG. 4f, a time and date stamp is also affixed.

Figure 4G:

If the signer rejects the signature by clicking the appropriate button, a confirmation screen as depicted in FIG. 4g may be presented. In a preferred embodiment, a list may be provided to the signer of common reasons for rejection, such as the signer not being an appropriate person to sign the document. In one embodiment, rejected documents may store a notation, such as a hash mark, in the signature region.

The interface depicted in FIGS. 4a-f may allow the signer to cycle through a number of documents very quickly, thus enabling efficient and high speed review of documents and collection of necessary signatures.

Figure 5:
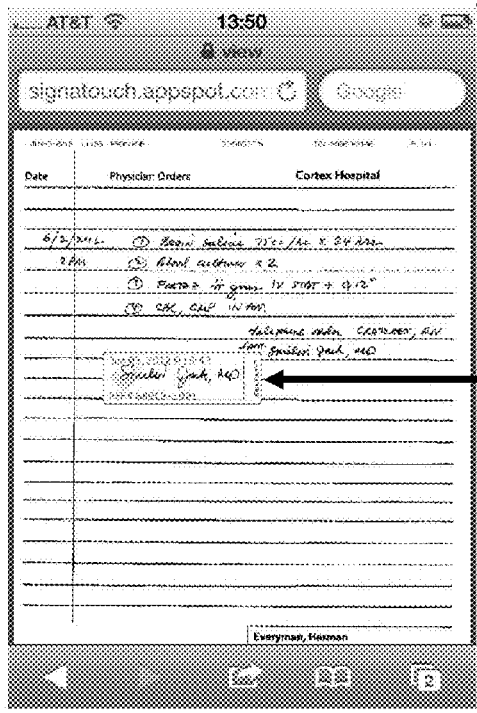
FIG. 5 depicts a document after the pre-validated signer's signature has been affixed in accordance one embodiment of the present disclosure.

Once a signer has authorized his or her signature, the signer's electronic signature is stored within the document as shown in FIG. 5

Figure 6A:
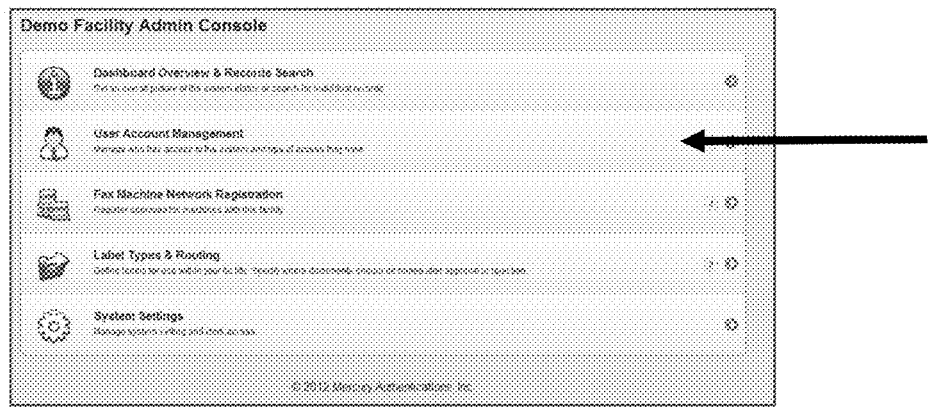
FIGS. 6a-j depict a series of interfaces which may be displayed during the account creation process in accordance with one embodiment of the present disclosure.
Figure 6B:
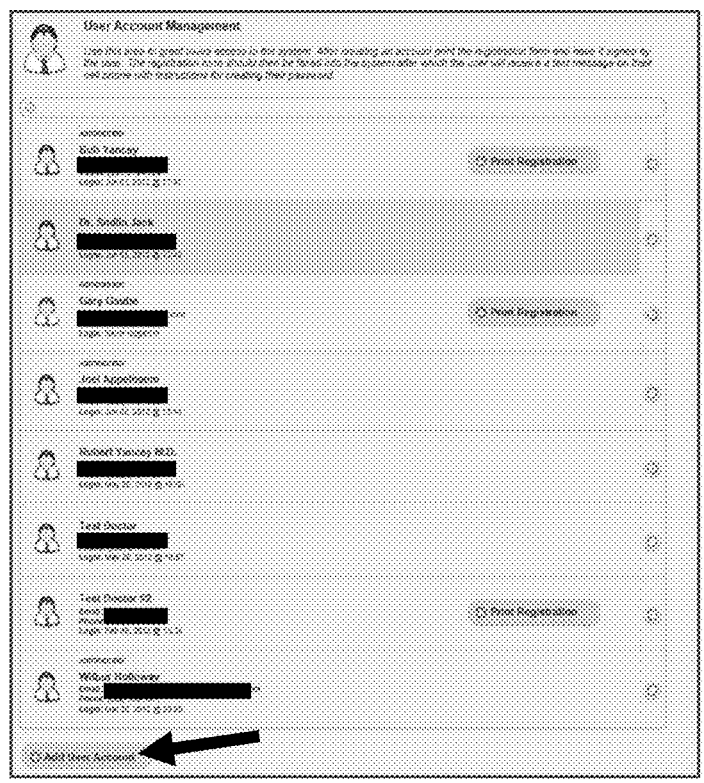

FIGS. 6a-j depict illustrative screens that may be presented when adding a pre-validated signer. A dashboard management interface may be displayed as shown in FIG. 6a. A user of the dashboard retrieve a list of validated users of the system as shown in FIG. 6b.

Figure 6C:
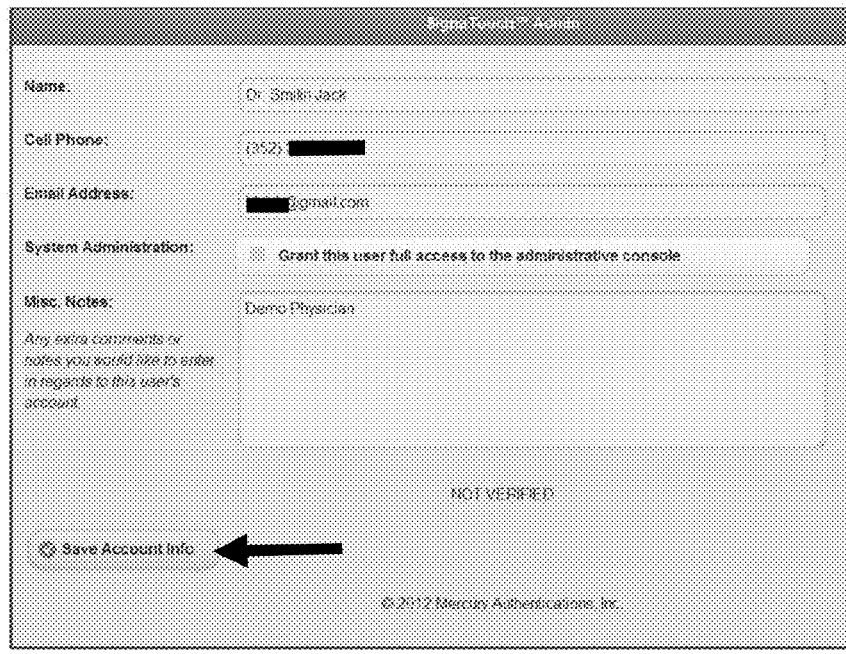
Figure 6D:
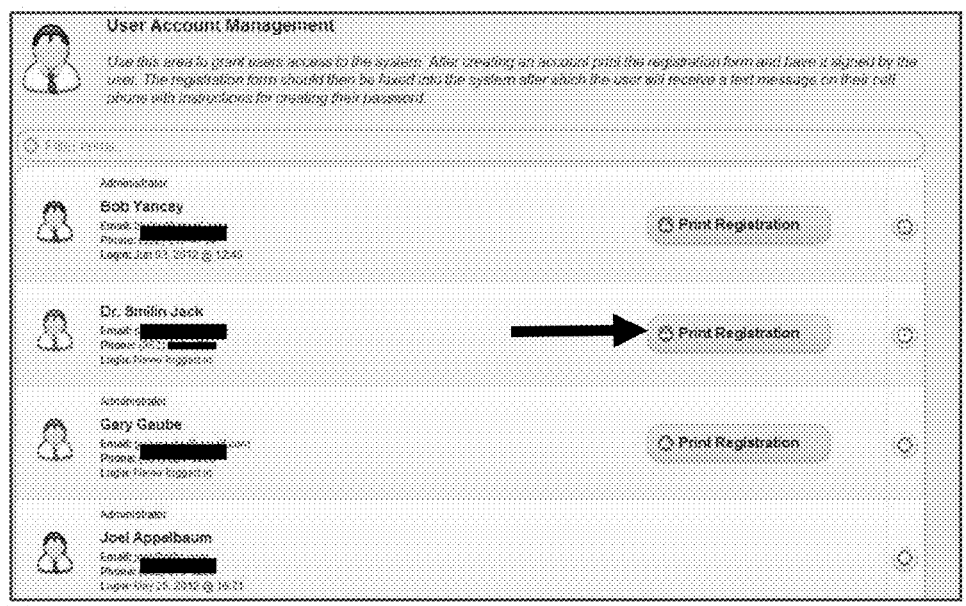
Figure 6E:
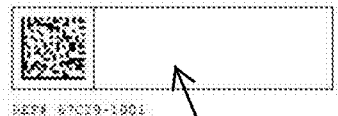

When adding a new user, certain user information may be collected as shown in FIG. 6c. Next, as shown in FIG. 6d, a registration form may be printed. The registration form, as shown in FIG. 6e, will be provided to the user and may be used to collect the user's signature in the signature region 602. The signature collected in the signature region 602 is preferably stored in a datastore. This signature is then affixed to documents signed in accordance with the present disclosure.

The datastore may be any system capable of storing electronic information, but is preferably a database. In one preferred embodiment, a noSQL database system is utilized. In another preferred embodiment, a sparse, distributed, persistent, multidimensional sorted map is utilized. In another preferred embodiment, a relational database system is utilized. In other embodiments, the datastore may be a flat file, an XML file, or a filesystem.

Figure 6F:
Figure 6G:
Figure 6H:
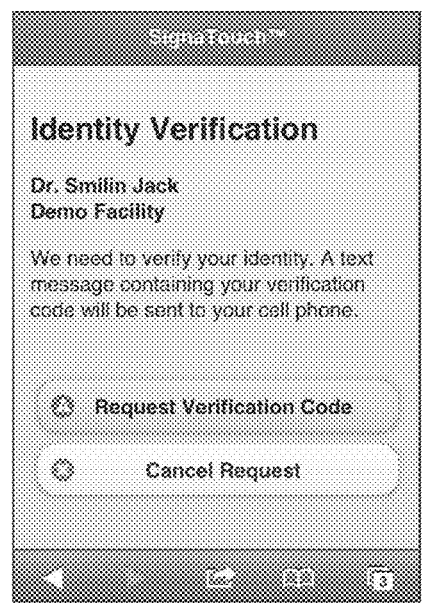
Figure 6I:
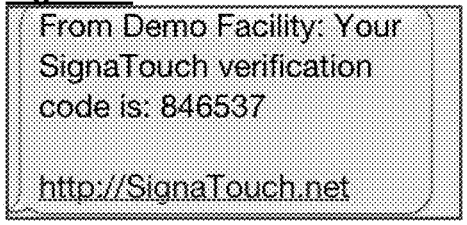
Figure 6J:
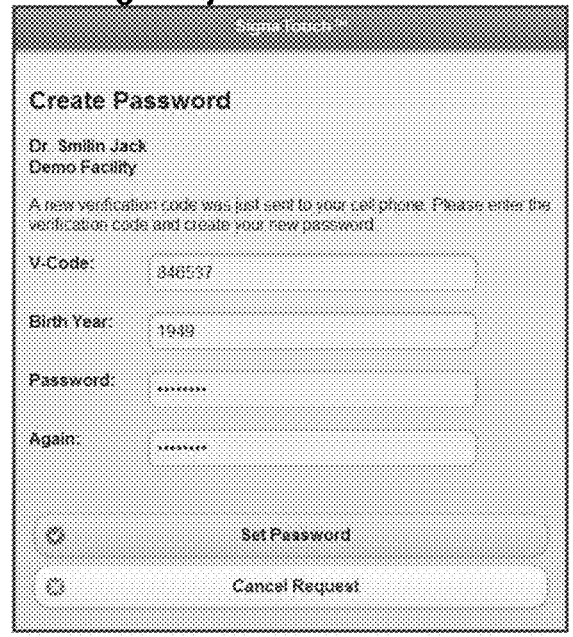

FIG. 6f shows the registration form executed by a user of the system. The executed form may be transmitted to the system via any electronic communication capability, such as by way of fax or as a scanned electronic document. In a preferred embodiment, the signature region 602 includes another machine readable area 604 so that the addition of new signers into the system may be automated.

Once the executed registration form has been received, an account verification process may take place as shown in FIGS. 6g-j. These screens help to insure the device to be registered actually belongs to the signer intending to register the device.

Users of the system other than pre-validated signers gain benefit from its features. For instance, FIGS. 7a-d depict some other capabilities, which may be presented in a separate mode of operation, for instance Clerical Mode as described in FIG. 7a.

In one embodiment, the Clerical Mode does not require a user to authenticate himself or herself. Instead, only certain pre-registered machines may be permitted to operate in such a mode. For instance, only network verified machines may be permitted to operate in such a mode. Such machines may be, for example, those machines on an internal network at a medical facility that are known to be protected.

Through this limited operational Clerical Mode, a user may be able to print reports, search the status of specific documents, or print new labels 100 for paper systems. Clerical Mode may not permit viewing of the actual documents so as to protect privacy.

Returning to FIG. 7b, a user may use a number of criteria to generate various reports. For example, the user may search for all documents sent to a particular device, such as a particular fax machine.

Figure 7A:
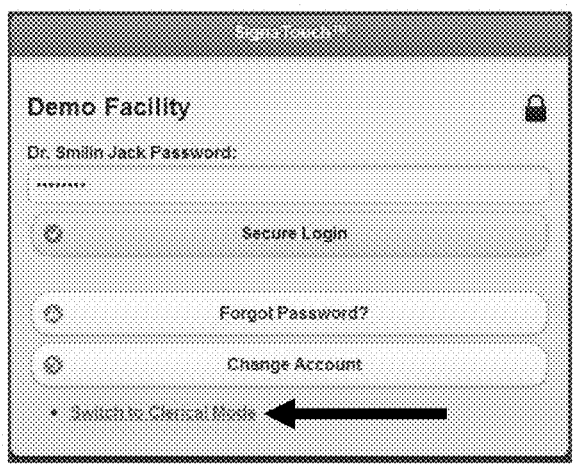
FIGS. 7a-d depict a series of interfaces which may be displayed in a clerifcal mode operation of a system in accordance with one embodiment of the present disclosure.
Figure 7B:
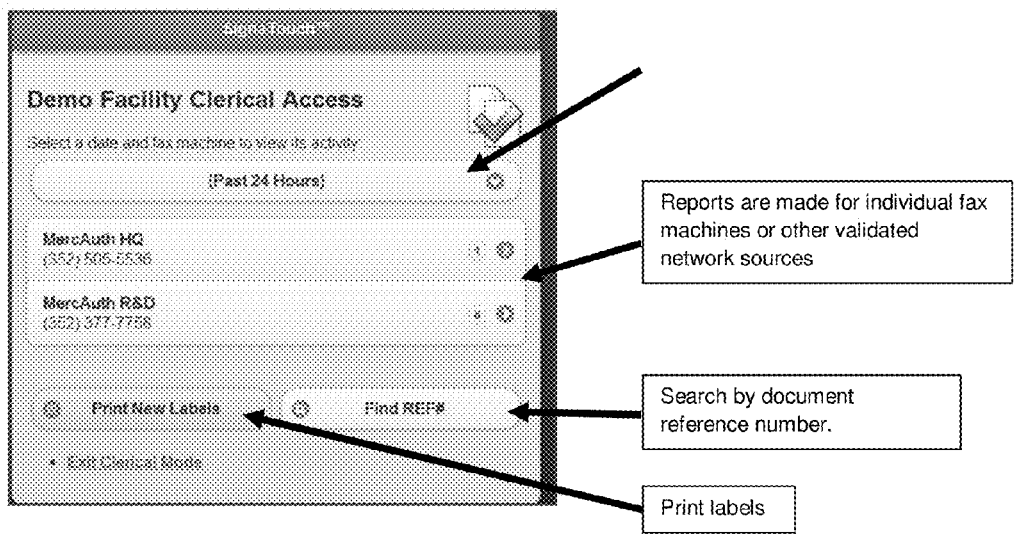
Figure 7C:
Figure 7D:

The user may also create additional labels 100, as shown in FIGS. 7c and 7d. The user may enter appropriate information, and the system will generate the proper type and number of labels 100.

Figure 8:
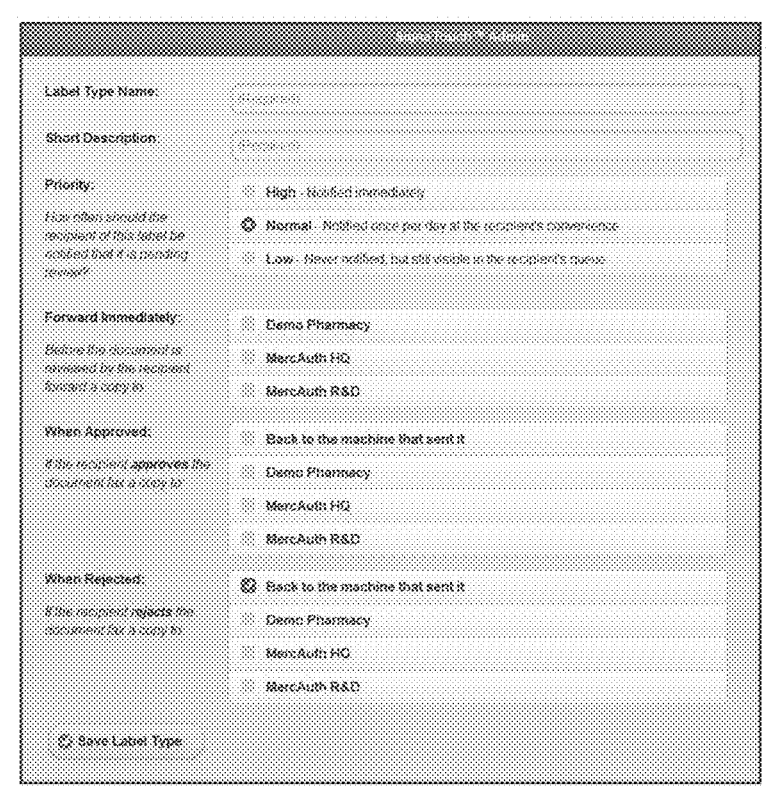

The system may also permit the user advanced design capabilities for designing the labels ads depicted in FIG. 8. Here, a user may customize paper or electronic labels to fit the particular needs. Once any device has been registered and validated with the system, that device may be used to generate new labels.

Additionally, a user may create more advanced routing directives. For example, a user may require that once a first person has signed a document, the document must be routed to a second person. This information is preferably stored in the datastore. Thus, when the system or method in accordance with the present disclosure receives the first signer's authorization, it may pass the document along to the next signer required to sign the document.

Figure 9:
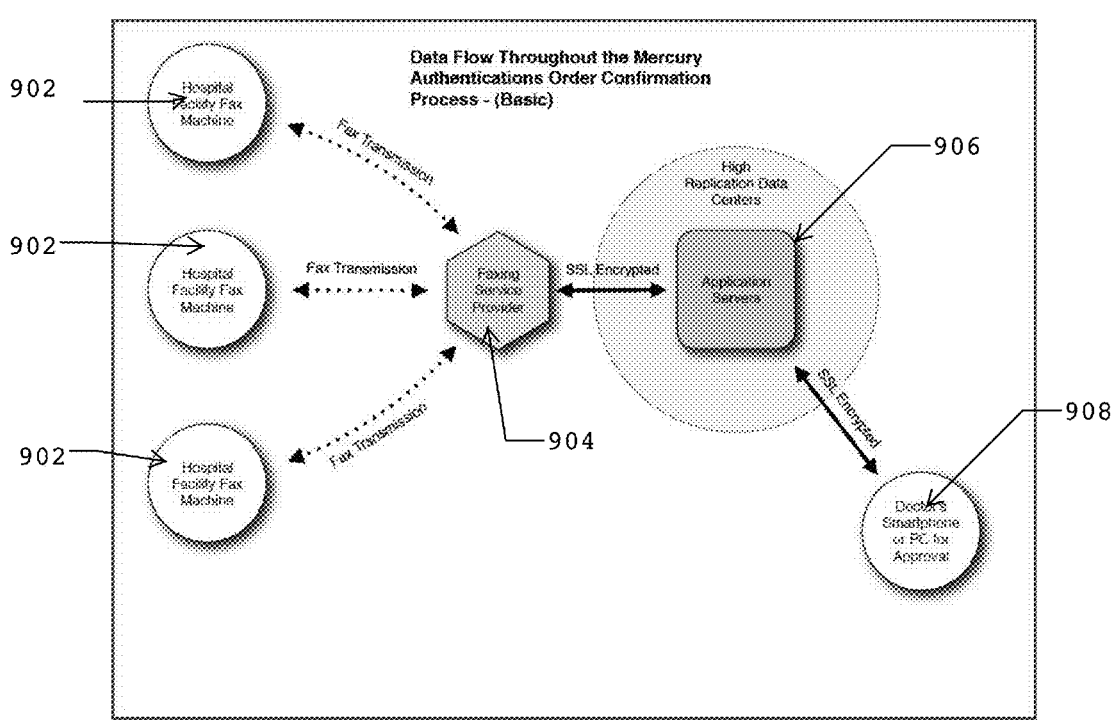
FIG. 9 is a chart depicting a data flow in accordance with one embodiment of the present disclosure.

FIG. 9 depicts a general dataflow pattern using a medical facility as a model in accordance with a preferred embodiment of the present disclosure. Documents to be signed may be faxed in accordance with the present disclosure from a number of hospital fax machine facilities 902. These paper-based documents requiring signatures may then be forwarded to a faxing service provider 904 which may direct the documents into the system in accordance with the present disclosure.

Communication between the faxing service provider 904 and the application servers 906 may be via any reasonable communication capability, including a network, intranet, local network, WIFI, Bluetooth, or other communication capability. Preferably, the communication is encrypted to protect the information in transit, and SSL is preferred.

The application servers 906 are configured to execute steps in accordance with the present disclosure. The system and method may be implemented on one or more computing systems, which can include a personal computer, a workstation, a network computer, a hand held computer, or any other computer system. Further, the system can be written as a software program in any appropriate computer language.

The system may preferably include a processing device, which can be any computer processing unit, and could be a central processing unit, or a number of processing units configured to operate either in sequence or in parallel. The processing device may be configured to execute software processes which implemented the steps disclosed herein. The system may also include a memory capable of storing the steps necessary for a processing device to implement the steps disclosed herein. This memory could be in the form of memory resident within the processing device or in the form of standalone memory coupled to the processing unit via a communication path, such as a bus or a network.

Application servers 906 communicate with the pre-validated signers through the devices 908 previously registered. Preferably, this communication is also encrypted, with SSL being preferred.

Figure 10:
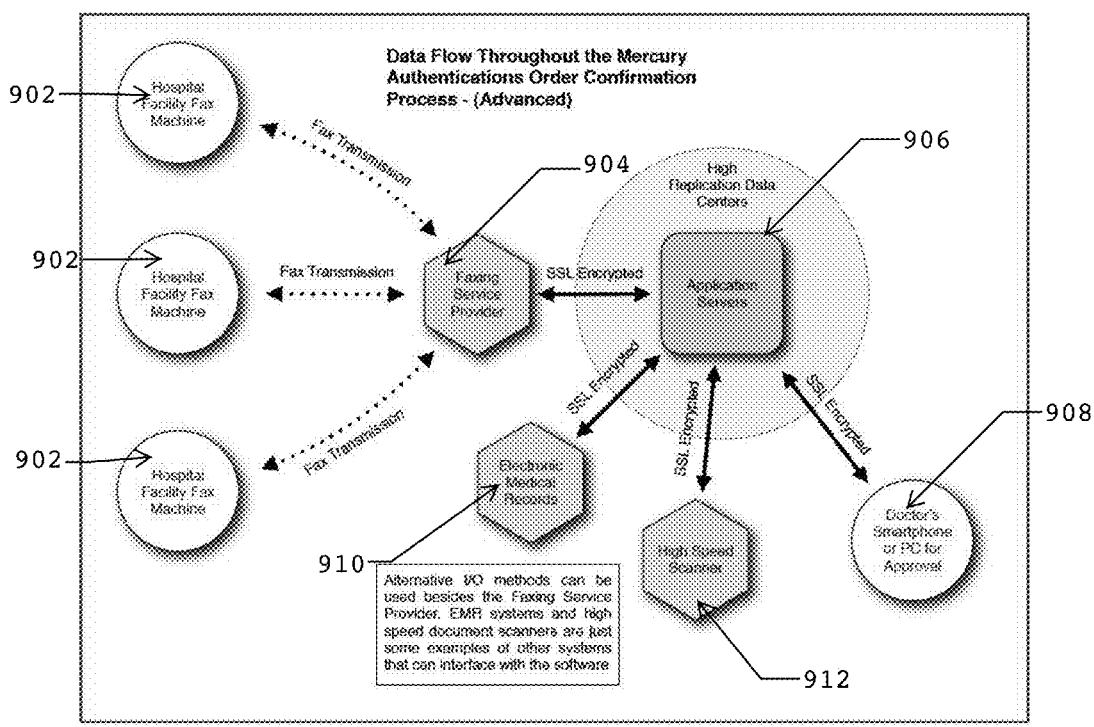
FIG. 10 is a chart depicting a data flow in accordance with one embodiment of the present disclosure.

FIG. 10 depicts the general dataflow in a system that uses Electronic Medical Records 910 or scanners 912 to enter data. In this scenario, paper-based documents do not need to be faxed, as they exist electronically either by way of being Electronic Medical Records 910 or by being scanned 912. Any other capability for creating electronic documents may also work. As with FIG. 9, communications are preferably via SSL.

Figure 11A:
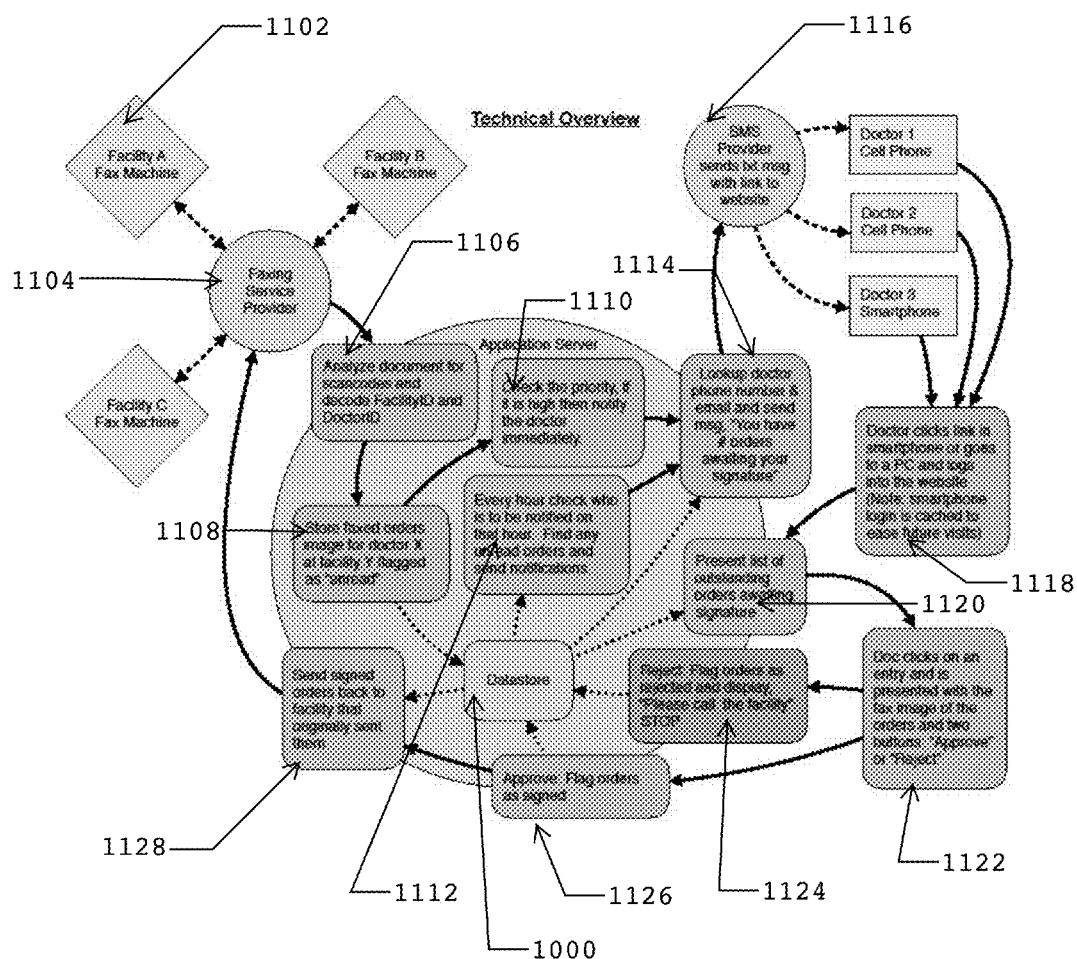
FIGS. 11a-b are charts depicting data flow in accordance with embodiments of the present disclosure.

FIG. 11a depicts a general process flow for a paper-to-digital embodiment. Documents are faxed into the system via the fax machines 1102 and faxing service provider 1104. Appropriate labels 100 have previously been affixed to these documents prior to faxing. At step 1106, the documents are analyzed to determine which facility and which signer (doctor, or other provider) must sign the document. Once this determination has been made, the process continues to step 1108 where the document is stored to be signed by the appropriate individual. If the document is high priority, the document may immediately be sent along to the appropriate signing individual at step 1110. If not, the system may wait until the appropriate interval to send the document along to the signing individual as shown at step 1112.

At step 1114, the system must determine how to send the authorization request to the signing individual, thus the system looks up this information. Preferably, the information is stored in the datastore 1000. At step 1116, the system notifies the signing individual that there are documents requiring signature.

At steps 1118 and 1120, upon receipt of the notification, the signing individual (the doctor) authenticates himself or herself with the system, and is then presented a list of documents to be signed.

The signing individual may then authorize or reject the pending documents at steps 1122, 1124, and 1126. When the signing individual approves the document (step 1126), the information is recorded (preferably in the datastore 1000), and then the signed document may be sent back to the original facility at step 1128. In a preferred embodiment, the signed document that is sent back includes a copy of the signing individuals signature as previously recorded when the signing individual registered with the system.

The datastore 1000 may be a single universal datastore, or each facility may have its own datastore 1000. Additionally, the datastore 1000 may be implemented on a single machine, or may be implemented on a number of machines.

Figure 11B:
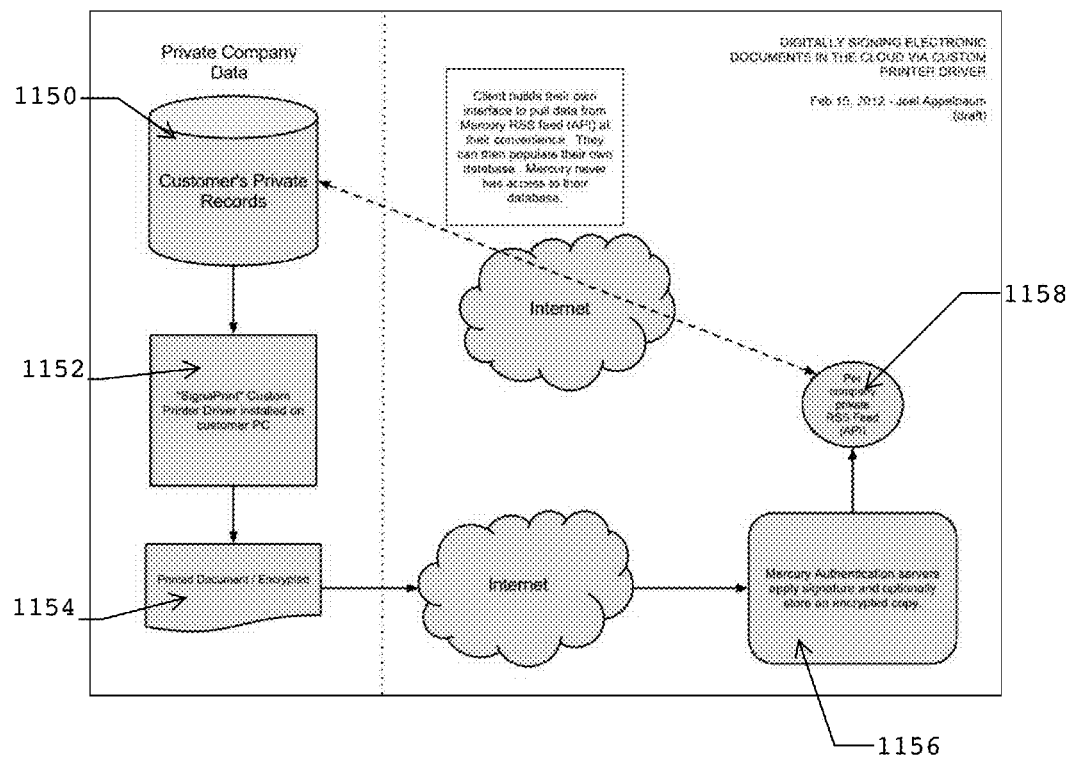

FIG. 11b illustrates a representation of an embodiment of the present disclosure whereby a customer's records are stored in a first database 1150. In this embodiment, the customer utilizes a specialized print driver 1152, which generates an appropriate electronic version of the document to be signed. The electronic version of the document to be signed may also preferably be encrypted at 1154 prior to being sent via a network.

Application servers at 1156 in combination with Application Programming Interfaces 1158 may be utilized to combine the functionality of the present disclosure with the customer's specific needs. In such a configuration, the customer may store its data privately, and separate from the datastore required to manage the signature process in accordance with the present disclosure.

Figure 12A:
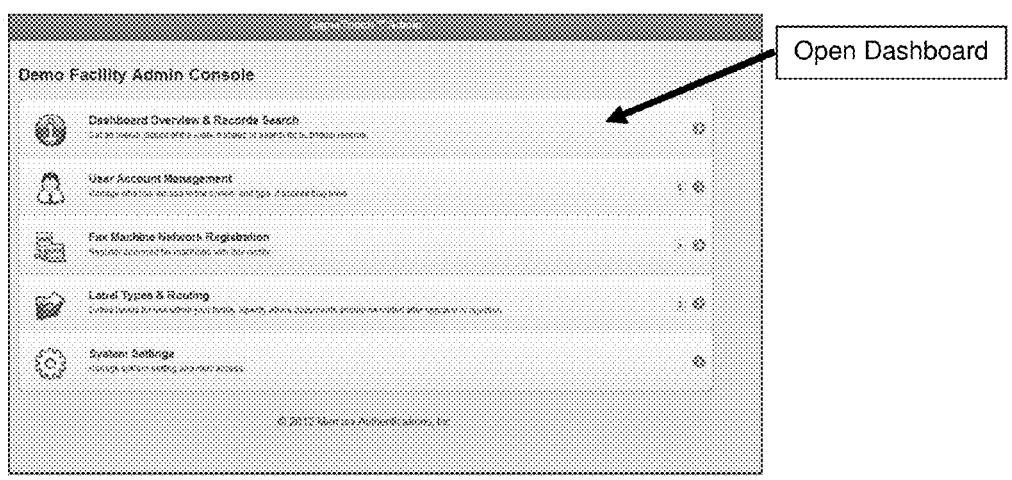

FIGS. 12a-d illustrate various interfaces which may be available in a system in accordance with the present disclosure. FIG. 12a depicts a dashboard screen, which may include record search, account management, fax machine registration, label type and routing, and other system settings.

Figure 12B:
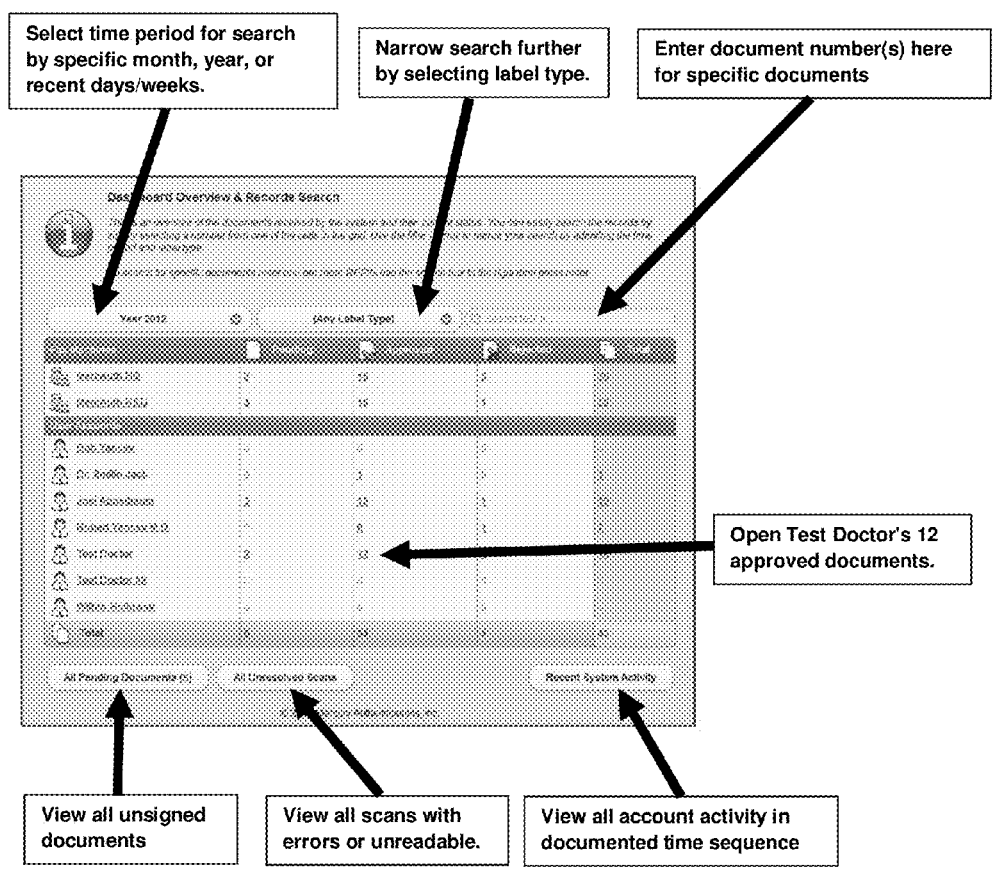

FIG. 12b depicts an interface that may be utilized for searching for documents. A user may be presented a number of search criteria, including time period, label type, document number, document status, errors, or other search criteria.

Figure 12C:
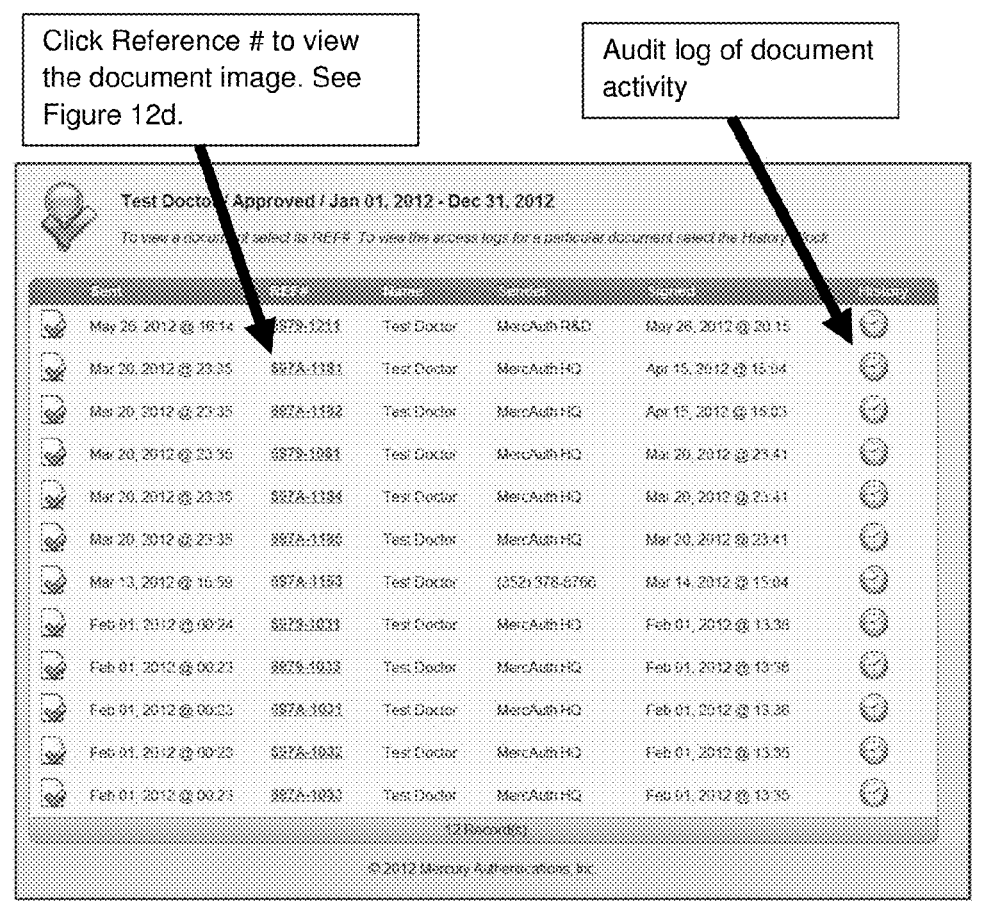
Figure 12D:
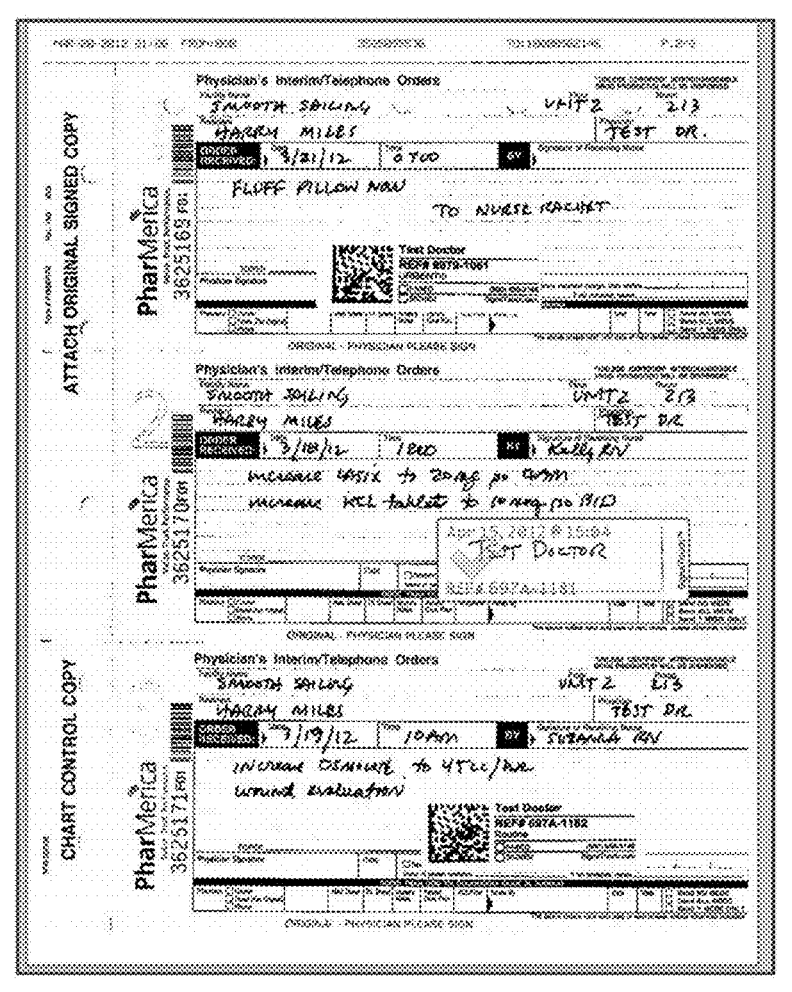

FIG. 12c illustrates an exemplary screen enabling an administrator to further analyze the status of particular documents. Clicking on one of the documents may present a screen such as depicted in FIG. 12d. As the document depicted in FIG. 12d has been signed, the image presented includes the signing individual's signature ("Test Doctor") as well as a date stamp (Apr. 15, 2012@ 15:04) corresponding to when the signature was approved.

In another embodiment, a user may track a paper document utilize a scanning device. The scanning device may preferably be a smartphone configured to scan a label 100 on the paper document, but could be any sufficient scanning device. The scanning device may first preferably require the user authenticate himself or herself with the system. The scanning device would then interface with the datastore to gather information related to the respective label 100. Through this embodiment, users may track the progress of document signatures using either the administrative control panel or by way of a handheld scanning device.

In one embodiment, upon scanning a paper document with the scanning device, a lookup is performed in the datastore, returning whether or not the signature was approved, rejected, or not found. The lookup may also return time and date information associated with the signature process, for instance when the signature was approved or rejected. If the document is found, a link may also be provided permitting the user of the scanning device to view an electronic version of the document.

In another embodiment, the label 100 may include a radio frequency identifier (RFID). In such an embodiment, the RFID may be utilized by the scanning device to scan a plurality of documents at once. The scanning device in such an embodiment would be capable of reading the RFIDs to gather the necessary information.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A digital signature method for collection of signatures from pre-validated signers, the method comprising:
   storing in a datastore a pre-validated signer's signature and a device the pre-validated signer has authorized for receiving signature requests;
   creating a label, the label including a unique identifier wherein the identifier is stored in the datastore;
   affixing the label to the paper document to be signed;
   creating an electronic copy of the paper document;
   determining from the datastore a pre-validated signer required to sign the electronic copy of the paper document;
   securely transmitting the electronic copy of the paper document to the device the pre-validated signer has authorized for receiving signature requests;
   receiving from the pre-validated signer's device an electronic acknowledgement authorizing use of the pre-validated signer's signature;
   retrieving the pre-validated signer's digital signature from the datastore; and
   affixing the pre-validated signer's digital signature to the electronic copy of the paper document.

2. The method of claim 1 wherein the datastore is a database.

3. The method of claim 1 wherein the datastore is a plurality of databases.

4. The method of claim 1 wherein the label includes a barcode.

5. The method of claim 1 wherein the label includes a 2D code.

6. The method of claim 1 wherein the label comprises:
   a pre-validated signer's name;
   the unique identifier; and
   a priority indicator.

7. The method of claim 1 wherein the device the pre-validated signer has authorized for receiving signature requests is a smartphone.

8. The method of claim 1 wherein the device the pre-validated signer has authorized for receiving signature requests is a facsimile machine.

9. The method of claim 1 further comprising:
   after receiving the pre-validated signer's electronic acknowledgement, determining from the datastore a second pre-validated signer required to sign the electronic copy of the document.

10. The method of claim 1 wherein affixing the pre-validated signer's digital signature to the electronic copy of the paper document comprises embedding the pre-validated signer's digital signature in the document in a location corresponding to the location in which the label was affixed.

* * * * *